United States Patent
Frangi et al.

[11] Patent Number: 6,156,001
[45] Date of Patent: Dec. 5, 2000

[54] GARMENT OR SANITARY PROTECTION MADE OF AN ELASTIC FABRIC DIRECTLY ENGAGEABLE BY "VELCRO" FASTENERS

[75] Inventors: Giampietro Frangi; Gianluigi Frangi, both of Varese, Italy

[73] Assignee: Pavis Varese S.R.L., Varese, Italy

[21] Appl. No.: 09/381,242

[22] PCT Filed: Mar. 17, 1998

[86] PCT No.: PCT/IT98/00054

§ 371 Date: Sep. 17, 1999

§ 102(e) Date: Sep. 17, 1999

[87] PCT Pub. No.: WO98/46175

PCT Pub. Date: Oct. 22, 1998

[30] Foreign Application Priority Data

Apr. 16, 1997 [IT] Italy .................................. YA97A0012

[51] Int. Cl.[7] .................................................. A61F 13/00
[52] U.S. Cl. ................. 602/75; 602/19; 602/21; 602/26; 602/60; 602/62; 602/63; 602/65
[58] Field of Search ................. 602/19, 20, 21, 602/23, 27, 60, 62, 63, 64, 65, 74, 75, 76, 79; 2/455, 456, 24, 170; 428/99, 224, 230, 231, 252, 253, 258, 259

[56] References Cited

U.S. PATENT DOCUMENTS 5,139,479  8/1992  Peters .......................................... 602/27
5,382,466  1/1995  Ingham ...................................... 428/219
5,472,413  12/1995  Detty ........................................... 602/26

FOREIGN PATENT DOCUMENTS 2089850  6/1982  United Kingdom ................. 622/75 X
9219201  11/1992  WIPO ..................................... 602/19

*Primary Examiner*—Kim M. Lee
*Attorney, Agent, or Firm*—Pollock, Vande Sande & Amernick

[57] ABSTRACT

An elastic textile implement to be tightly worn over an articulation or part of the body to be protected and/or aided in its mechanical action is made in a geometrically flat form foldable to shape, substantially of a single size. The implement is made in the form of a planar made of an elastic fabric comprising an elastomeric yarn and substantially non-elastic yarns, conformable around said part or articulation and tautingly fixed thereon by "Velcro" ® fasteners, the fabric comprising at least a third substantially non-elastic yarn of a material selected from the group composed of nylon, polyester and mylar, interwoven with at least a first and a second non-elastic yarns and with said elastomeric yarn and forming a dense population of loops (M) projecting for a determined height out of one face of the fabric. "Velcro" ® fasteners with tiny hooks are sewn on a plurality of independently stretchable edge portions of said implement, each edge portion being superimposable to the outer surface of the fabric having said population of loops (M) and anchorable in any position.

6 Claims, 6 Drawing Sheets

GARMENT OR SANITARY PROTECTION MADE OF AN ELASTIC FABRIC DIRECTLY ENGAGEABLE BY "VELCRO" FASTENERS

The present invention relates to garments and sanitary protections which can be tightly worn on a body part or articulation to be protected or aided in its mechanical action. The invention is particularly useful for making ankle-bands, leggings, knee-bands, general purpose elastic belts, elastic wrist bandages, special outfits for sport and other highly technical activities, speed outfits, etc.

In making elastic sanitary implements for aiding the mechanical action of articulations, in order to recover their full functionality after injuries or as a form of prevention in performing sporting activities involving relatively high stresses on muscles and/or articulations, it is necessary to ensure, besides the comfort of use, a good adjustability of the elastic tautness.

The conventional tubular elastic sanitary protections are obviously not capable of satisfying the adjustability requirement and can be produced only in a series of relatively standardized sizes.

For uses absolutely requiring the possibility of adjustment, both for the effectiveness of the elastic guard and for comfort, a common lacing must be used for joining two opposite edges of an elastic sanitary band or garment so as to allow to control the tautness and/or to modulate it along its length. The adjustment of the tautness by loosening or tightening the lacing is a wearisome and not very practical operation. In order to obviate the laboriousness of a lacing, use is often made of the so-called "Velcro" ® wherein a strip material having a population of tiny hooks fasteners on surface is sewn onto an edge of the sanitary protection, garment or footwear and may be pressed into an anchoring engagement on the surface of a cooperating strip of piled fabric. The range of adjustment of the tautness depends obviously upon the size of the area of piled fabric available for anchoring the hooked part of the "Velcro", that is either sewn over the opposite edge of the elastic implement or on the same edge thereof, in which case the band of "Velcro" with the tiny hooks is first passed through a eyelet of the opposite edge of the implement and pulled back to anchor it on the sewn pad of piled fabric. In case "Velcro" fasteners are used for closing and tightening a substantially tubular sanitary protection or garment, the proper positioning of the sanitary protection around the articulation to be protected is made difficult by the need of elastically stretching one edge only of the implement before joining the two cooperating parts of the "Velcro" fastener, often resulting in accidental slippings of the sleeve or bandage, which must be repositioned after fastening it.

When, as it is often the case, these sanitary implements, bandages or garments are wholly or at least partially made of an elastic fabric comprising textile yarn of a natural or synthetic fiber, interwoven by knitting or other suitable weaving techniques with elastomeric yarns so as to produce an elastic fabric, paddings of a suitable fabric (pile) must be applied in the areas where the hooked Velcro material, sewn in proximity of a superimposable edge of the elastic fabric may be anchored. This need to provide for suitable "Velcro" anchoring pads arises from the fact that the elastic fabric cannot withstand repeated engagements with the tiny hooks of the "Velcro" material, which would quickly and irremediably damage the elastic fabric.

On the other hand, the need to have "Velcro" anchoring pads of a suitable pile sewn on the outer surface of the elastic implement implies the presence of local bumps and stiffenings which may have wearisome outcomes, especially in case of prolonged use of these implements for dynamic activities.

Furthermore, a predefined position of these anchoring pads "Velcro" limits the possibility to adjust tautness of the garment or sanitary protection and retail shops of these implements must keep an adequate stock of different sizes.

When, as it often occurs, the sanitary implement comprise stiffeners or reinforcements permanently or removably inserted into dedicated pockets or housings, the ability of an elastic bandage of a certain size to fit different situations (sizes) is even more reduced, in spite of an ability to stretch. In fact, the requirement of properly positioning of such stiffeners or supports with respect to the articulation or limb to be supported or immobilized practically makes the implement hardly suitable to fit body conformations or even marginally different sizes, thus forcing, especially in these cases, to keep a large stock of close sizes.

The keeping of large stocks of differently sized articles has a precise cost in terms of working capital tied up, which is especially critical for specialized commercial enterprises with a relatively small volume of business.

It is evident the need and/or the great usefulness of elastic sanitary protections, bandagings, garments and alike implements, comprising or not functional stiffeners or supports, tightenable by means of "Velcro" fasteners, capable of effectively fit different body conformations and sizes while ensuring a most appropriate configuration and more easily worn than the articles known nowadays.

This important objective to provide for an elastic sanitary implement of a substantially "monosize" character and combining this general ability to fit different body sizes to an enhanced practicality of use without having undesirable disuniformities in the elastic and foldability properties of the fabric, is achieved by making such an elastic sanitary implement or garment according to the present invention.

According to a first and important aspect of this invention, an elastic sanitary protection or guard or garment or alike implement that can be tightly worn over a part of the body or articulation to be protected or aided in its mechanical function, consist of a conformable piece of elastic fabric, composed of at least a first component fiber having a relatively fine DECITEX figure, for example $\geqq 120$, and more preferably $\geqq 200$, which is constituted by a monofilament or more preferably by a relatively small number of filaments, for example $\geqq 10$, of a synthetic material, such as nylon$^{TM}$, rayon$^{TM}$, mylar$^{TM}$, polyester or equivalent materials having a high tensile strength and a high abrasion resistance, interwoven with at least a second component or textile yarn, and with at least a third component or elastomeric yarn.

Such a first component interwoven with the other components, forms a dense population of eyelets or coils that projects in a perpendicular direction from one face of the elastic fabric, for a height generally comprised between 1 and 3 mm. Such a multitude of coils is present uniformly throughout the face of the elastic fabric and provides an appropriate anchoring structure for a piece of "Velcro" material with tiny hooks without being subject to defibrations or pile uplifting even by repeated and stressed engagements with the hooked "Velcro" material, substantially on any area that may be reached by stretchingly pulling an edge of the elastic fabric provided with the hooked "Velcro" material over the outer surface of the textile elastic implement.

Practically the whole outer surface of the sanitary bandage or garment made with such a composite elastic fabric is adapted to engagement with a hooked "Velcro" material, thus providing for an almost unlimited adjustability of the elastic implement, which thus may be worn in a perfectly adjusted tautness irrespective of the user's size.

Stiffeners or reinforcements that may be optionally associated to an elastic bandage in order to impart specific properties to the sanitary implement of elastic fabric for effectively supporting and/or immobilizing a joint, may be conveniently fastened in a removable fashion to the outer side of the elastic textile implement, precisely in the most functionally suitable position, after fixing the implement in place, by fastening with a "Velcro" piece the stiffening member on the outer surface of elastic fabric. This important functionality may be obtained simply by providing the assembly face of the reinforcing member or of its own textile sheath, with a strip of hooked "Velcro" material. This permits to fasten securely onto the fabric of the sanitary implement after having positioned and stretchingly tightened it over the joint articulation or muscles to be protected or aided.

Moreover, the basic elastic textile implement may be made without any pocket and/or portions applied by sewing extra pieces of fabric thereon, thus avoiding the related limitations and drawbacks.

These and other advantages of the implements made according to the present invention will become even more evident through the following description of several embodiments thereof, each intended for a specific use and by referring to the attached drawings, wherein:

FIGS. 1a, 1b, 1c and 1d illustrate the relevant weaving (knitting) motions of the various components yarns for producing the elastic textile structure provided with a surface population of eyelets for "Velcro" engagement;

FIG. 1e is a scheme of the functional members of the weaving machine.

FIG. 1a shows the operation carried out on the elastomeric yams 1 fed by the hook (crochette) A of FIG. 1e.

FIG. 1b shows the operation carried out on the warp yarn 2 fed by hook B of FIG. 1e.

FIG. 1c shows in the operation carried out on the inner (rear) weft yarn fed by the wefting tool C of FIG. 1e.

FIG. 1d shows the operations for forming eyelets M with the outer (front) weft yarn 4 fed by the wefting tool D and pulled by lancets E of FIG. 1e, in cooperation with needles F.

Figure 1A:
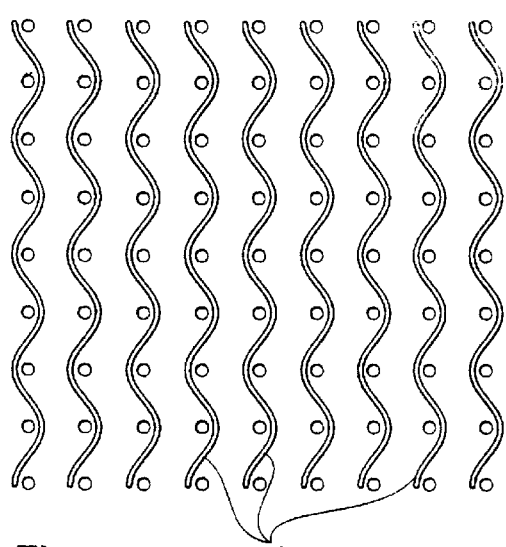
FIGS. 1a to 1e show schematically composite elastic textile structure that include a structure suitable for anchoring a hooked "Velcro" material.
Figure 1B:
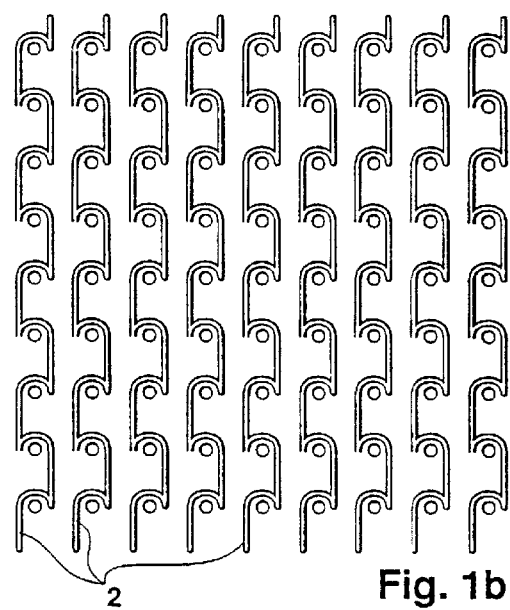
Figure 1C:
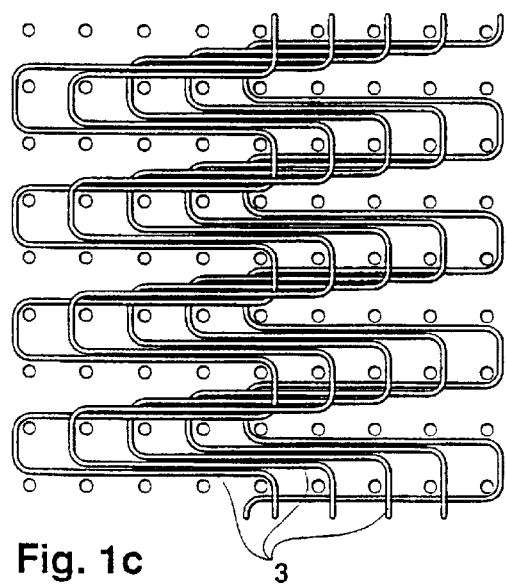
Figure 1D:
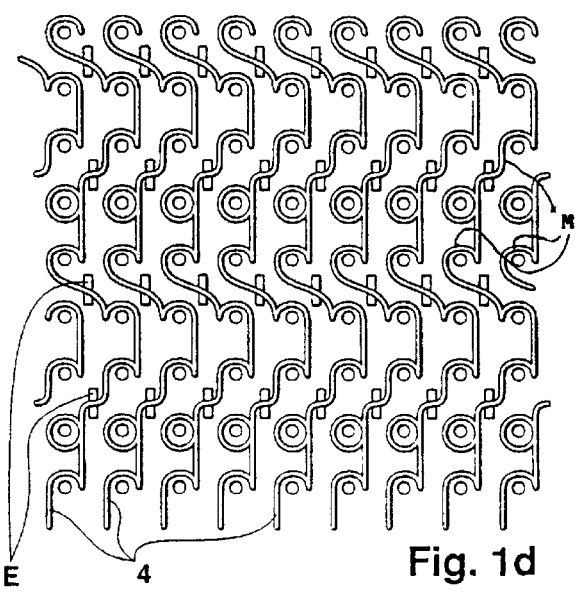
Figure 1E:
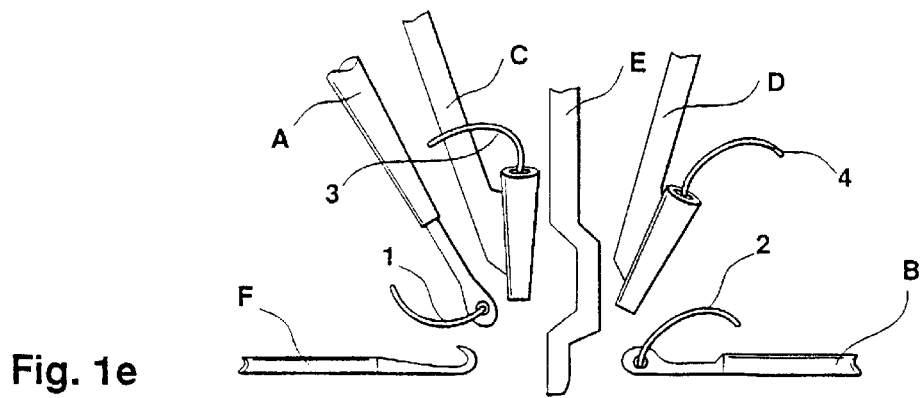

In a sample fabric, the various components had the following characteristics:

Elastomeric yarn: DECITEX count 1240. The number of hooks A is equal to the number of needles F.

Nylon 6.6 warp yarn: DECITEX count 78/23 *4. The number of wefting tools C is equal to the number of needles F.

Nylon 6.6 front weft yarn: DECITEX count 220/10 filaments. The number of wefting tools is equal to the number of needles F.

Nylon 6.6 rear weft yarn: DECITEX count 78/23 *4. The number of hooks B is equal to the number of needles F.

The fabric was knitted on a Raschel-Muller machine, Model RD3 SN/KSE, Fineness 6.

Warp yarn 2 and inner weft yarn 3 may obviously be made of a material other than nylon, e.g. of a suitable natural fiber. Front weft yarn 4, made of nylon with a fine,DECITEX count and a reduced number of filaments, may be as well a nylon monofilament yarn. It forms a dense population of eyelets or coils M that project out in a direction perpendicular to the face of the fabric, for a height that may generally be in the order of one to several millimeters.

The interweaving is such to retain to the fullest extent the elastic properties of the fabric, notwithstanding the formation of the "Velcro" anchoring structure on at least a fabric side by interweaving such a dedicated front weft component.

In this way, the elastic fabric may be engaged by "Velcro" fasteners without being significantly damaged by the tiny hooks thereof By adjusting the morphology of the tiny hooks of the "Velcro" material, namely by reducing their height and making them with a closer hook for better exploiting the presence of anchoring eyelets on the surface of the elastic fabric, the fabric withstand without any deterioration even the intrinsically harsh engagement with the hooked "Velcro" material, without any damage to the other components of the fabric, i.e. the textile yarns 2, 3 and the elastomeric yarns 1.

Figure 2:
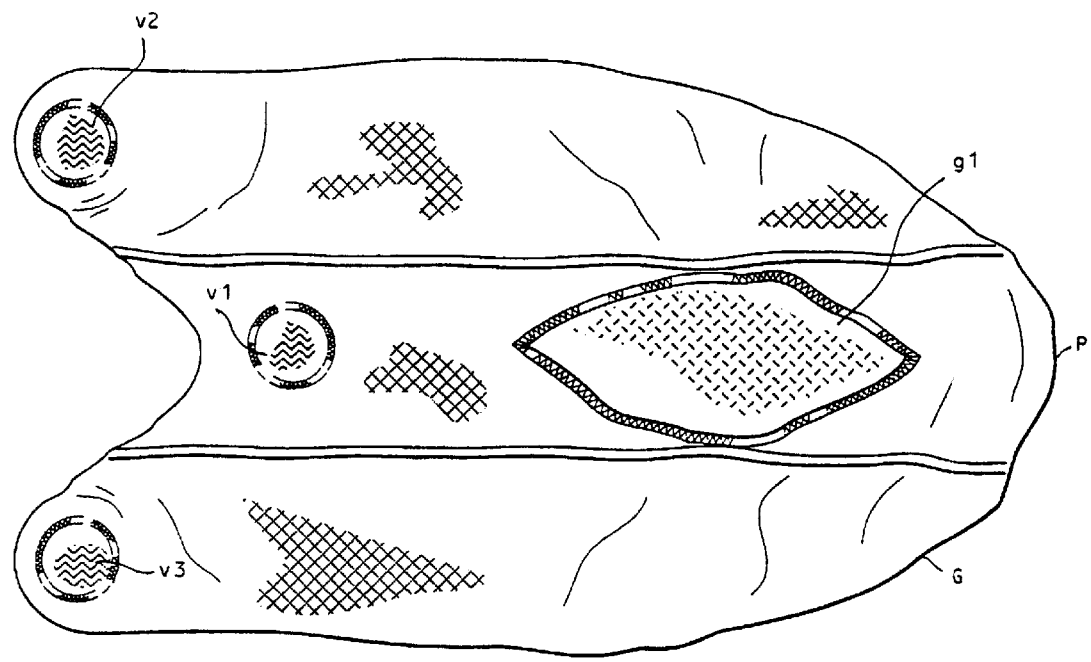
FIGS. 2 and 3 show a knee-band made according to the present invention.
Figure 3:
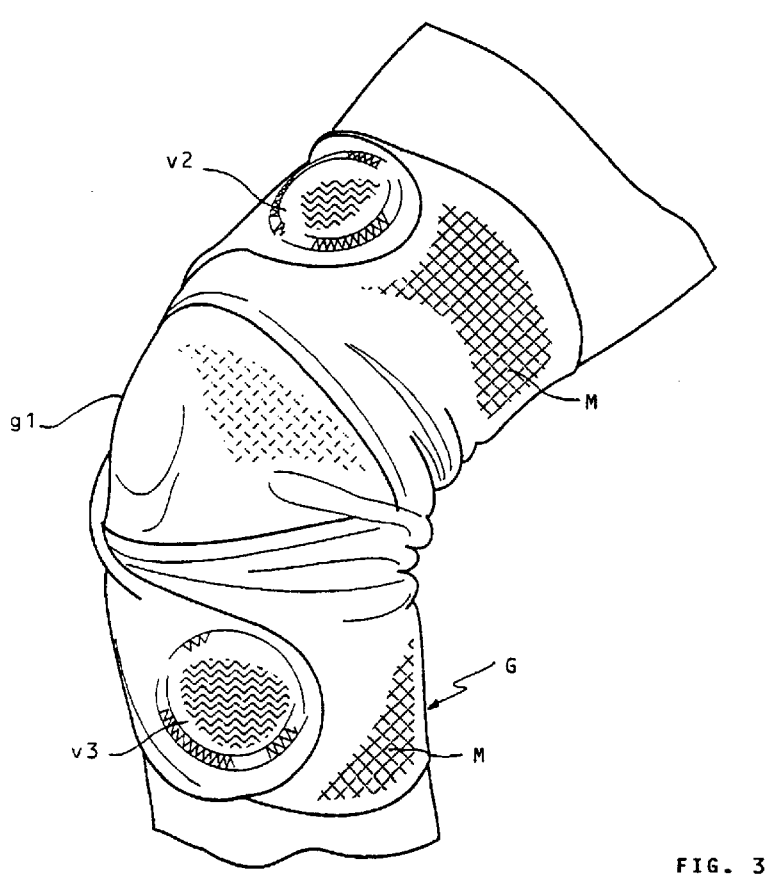

A knee-band G, made according to the present invention, structured as shown in FIG. 2, may fit perfectly a variety of sizes, and may be worn as depicted in FIG. 3.

Referring to FIG. 2, the knee-band G has a substantially planar structure and a shape vaguely similar to a spearhead or arrow feather. The "notched" (dovetailed) side represents the superimposable edge or tail of the elastic sanitary protection. In proximity of the two tip ends and of the notch vertex, the "inner" side has applied thereon (typically by sewing) three disks of hooked "Velcro" material v1, v2, v3. The knee-band G may be made entirely of a conformable composite elastic fabric of the aforementioned type, wherein its outer face has a structure that includes a population of coils or eyelets M made of a wear resistant nylon yarn. In the specific sample represented in FIG. 2, the knee-band G further comprises an elliptic-shaped diaphragm g1, of a common elastic fabric having a greater pliability than the fabric with which the rest of the knee-band G is made. Such an insert g1 may be positioned over the rotula in order to reduce locally the elastic stress exerted thereon by the knee-band.

The positioning and stretching of the knee-band are outstandingly simpler than with known sanitary products.

Indeed, it is sufficient to properly position the portion g1 on the top of the rotula by holding the knee-band with a hand while grasping with the fingers of the other hand the superimposable edge in proximity to the central "Velcro" disk v1 and to superimpose it over the edge being held fast with the other hand and press it into a fastening engagement on the outer side thereof (in proximity to tip p).

Once the knee-band has thus been blocked in position, the two superimposable upper and lower edges, may be easily and independently stretched, bringing the respective disks of "Velcro material" v2 and v3 into engagement with the outer side of the knee-band, independently adjusting more and more accurately their respective stretching.

As it is evident, all the three "Velcro" fasteners v1, v2, v3 are individually adjustable independently from one another, allowing a most comfortable modulation of tautness.

The elastic stretching may thus be accurately modulated, increasing it in critical spots, i.e. immediately above and below the articulation, by changing the point of anchorage of the different "Velcro" fasteners v2 and v3, which may be freely anchored in any portion of the outer surface of the knee-band of elastic fabric.

Figure 4:
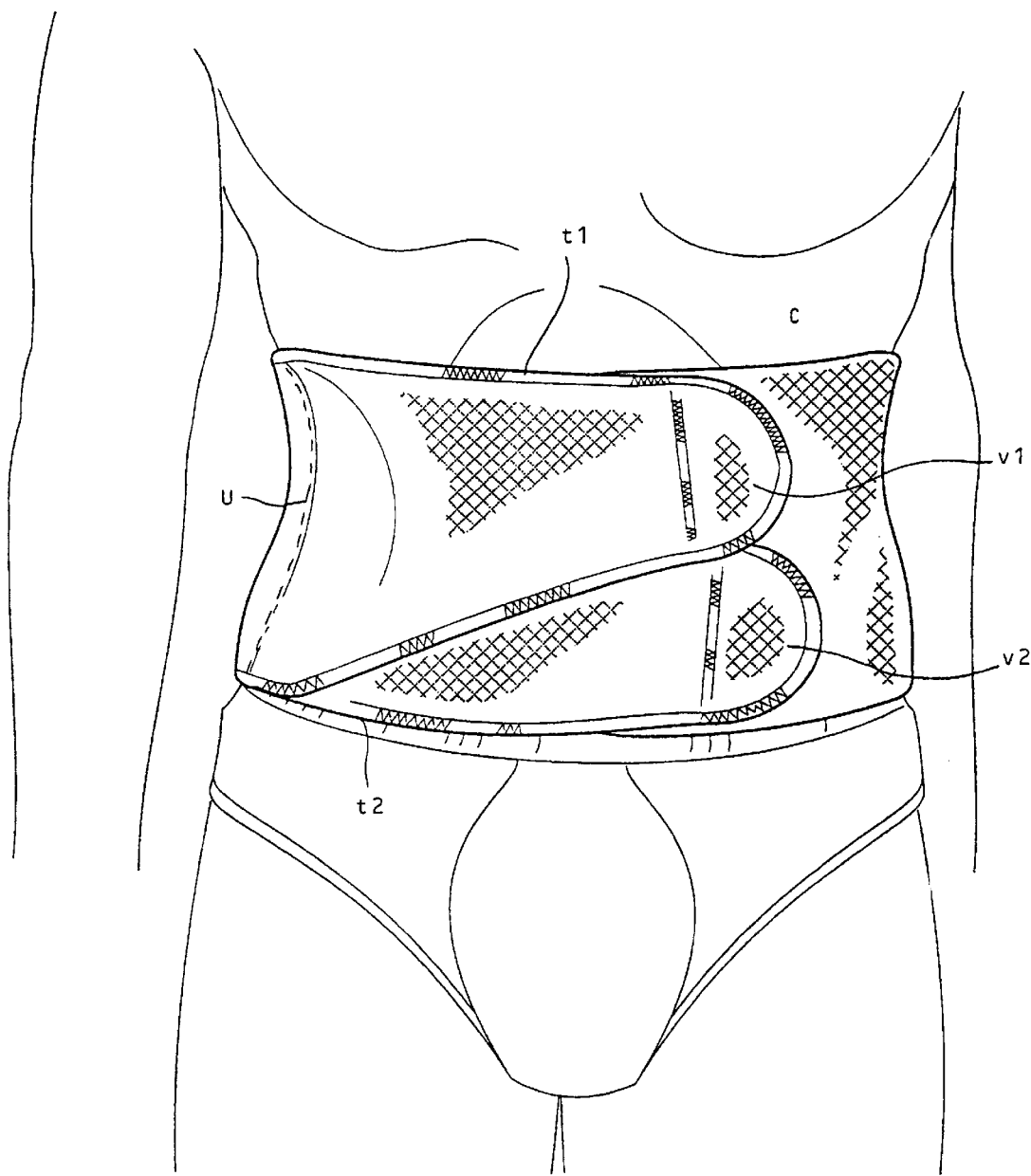
FIGS. 4 and 5 show an elastic belt made according to the present invention.
Figure 5:
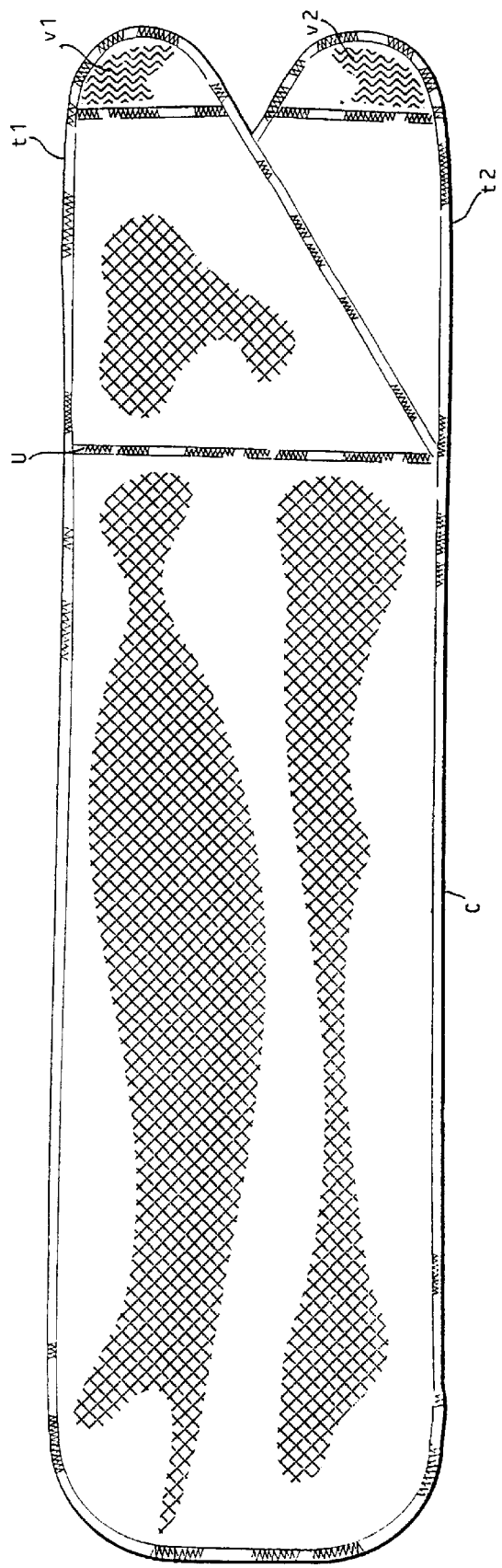
Figure 8:
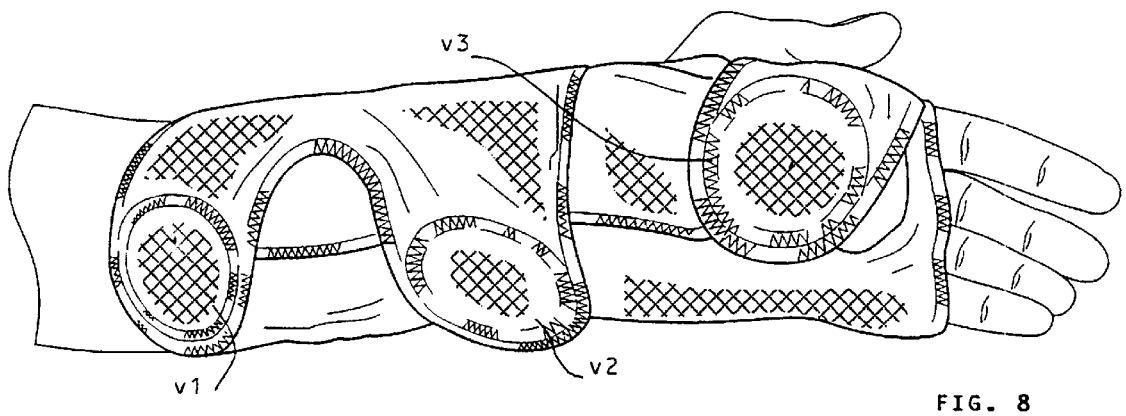
FIGS. 8 and 9 show a sanitary implement specially intended for immobilizing an injured wrist or hand.
Figure 6:
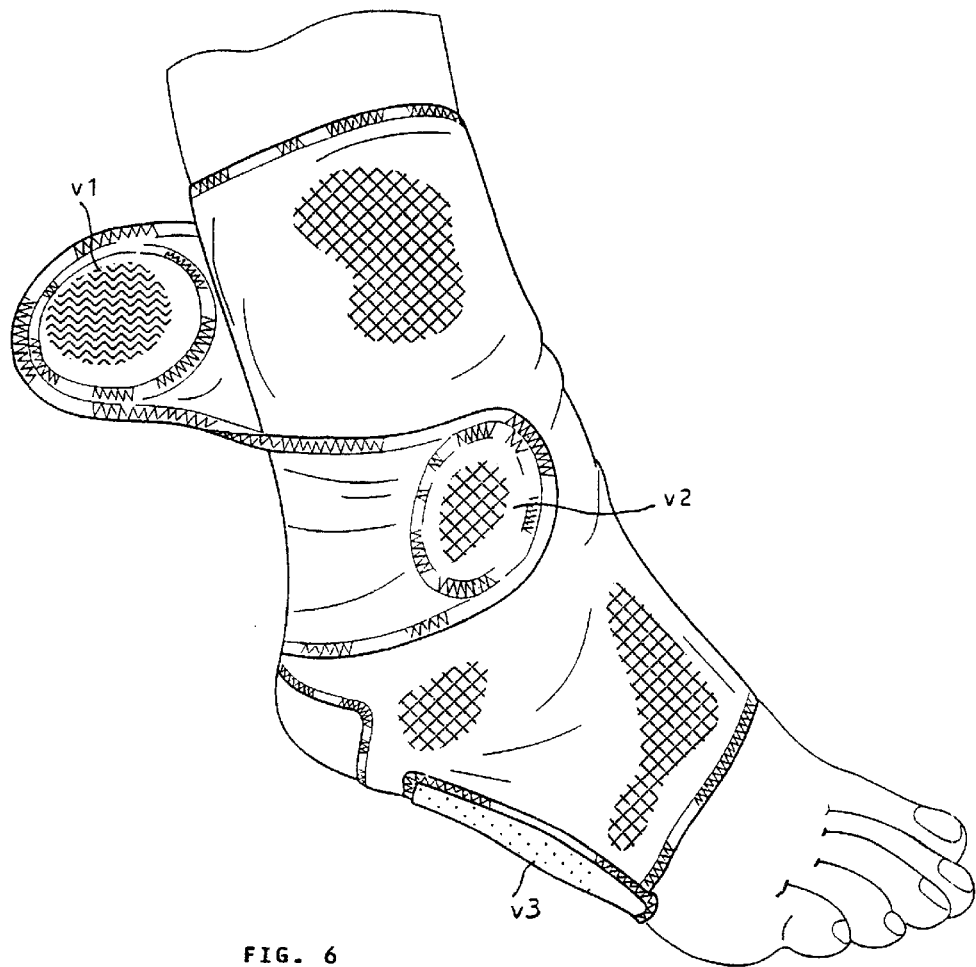
FIGS. 6 and 7 show an elastic ankle-band made according to the present invention.
Figure 9:
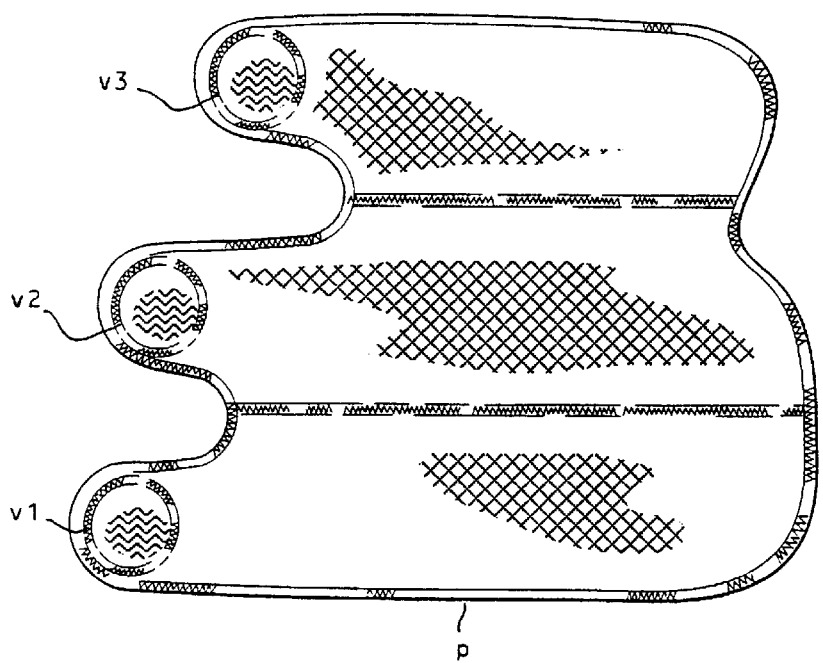
Figure 7:
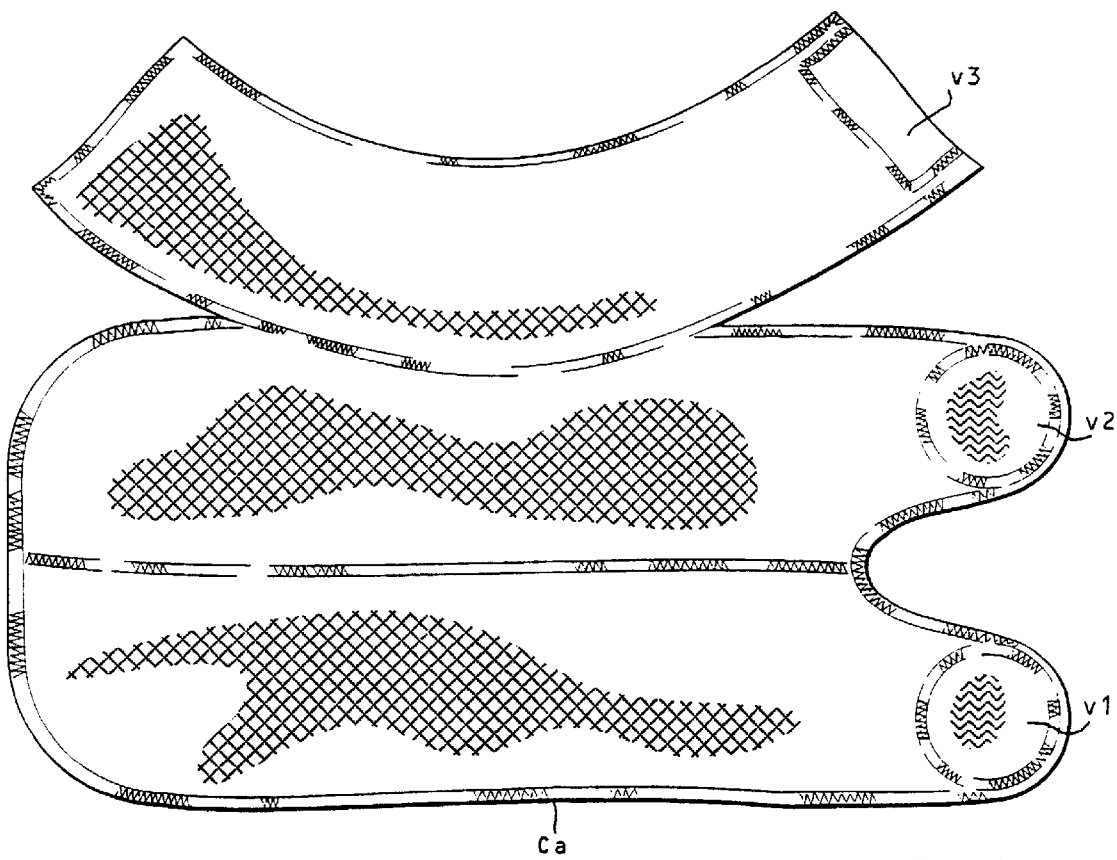

FIGS. 4 and 5 show an elastic belt C produced according to the invention by using the special elastic fabric of the invention capable of withstanding engagement with "Velcro" fasteners.

The belt structure is characterized in that one end thereof is made by joining two triangle-shaped, mutually independent tails t1, t2 along the junction line U, the remaining portion of elastic band being sufficiently long to allow the superimposition of the two triangular tails t1 and t2 on the outer face of the other end of the elastic band C.

The inner side of the elastic fabric of each triangular edge t1 and t2 has applied thereon, in proximity of its tip, a piece of hooked "Velcro" material, v1 and v2, which may be have a semicircular shape or any other shape.

It is immediately evident from FIG. 4, how to wear the elastic belt and how to adjust its tautness.

In fact, it is sufficient to place over the end of belt C, held fast with one hand, one triangular tail (t1 or t2) and to press its hooked "Velcro" piece into engagement in the desired point.

Then, it is sufficient to grasp the tip of the other triangular tail, stretch it and fasten its tip provided with the "Velcro" piece in the desired point, in order to get a comfortable tautness.

Also in this case, the ability of the belt to fit different sizes is evident by virtue of, the fact that the "Velcro" fasteners may be anchored at any point of the outer surface of the elastic fabric.

The adjustment of the elastic tautness may be independently varied for the lower and the upper parts of the belt to a certain extent, by changing the respective points of anchorage of the ends of the two triangular tails t1 and t2 of the elastic belt.

FIGS. 6, 7, 8 and 9 show an ankle-band and a band specially designed for wearing around a wrist and/or hand (wrist-band), both made according to the invention with an elastic cloth having a face that is engageable with hooked "Velcro" material.

Even in the case of these specific sanitary products, the unlimited possibility of superimposing three distinct fingers provided with hooked "Velcro" (v1, v2, v3) fasteners over the outer surface of the elastic fabric provided with a dense population of eyelets M, makes them capable of fitting a variety of sizes.

The division of the stretchable fabric into several parts (in the examples of FIGS. 6–7 and 8–9, into three distinct finger tail portions) superimposable on the rest of the fabric and the provision of distinct pieces of "Velcro" material (v1, v2, v3) at their ends, besides facilitating the positioning of the sanitary product over the joint, allows to modulate the elastic tautness by successively and repeatedly intervening on the distinct finger or tail portions provided with "Velcro" fasteners, independently from one another.

As the drawings show, the piece of elastic fabric, functionally cut to be worn around a certain articulation, may be cut as a single piece of elastic fabric and suitably edged, or tailored by joining two or more cut pieces of fabric together so as to optimize the functional shape and the elastic properties of the implement.

Should the elastic sanitary implement require reinforcing or stiffening members in precise locations in order to enhance their supporting action or for immobilizing the injured articulation, an effective positioning of such members in a sanitary implement according to the invention is made extraordinarily accurate and easy, by exploiting also in this case the ability of the entire outer surface of the elastic sanitary implement to provide for a fastening engagement with a "Velcro" material.

Instead of requiring the formation of pockets or housings into which the required stiffeners could be permanently or removably inserted, as in known implements, such stiffeners or paddings may be conveniently sheathed according to this invention into a textile sheath provided with a "Velcro" strip or several pieces of "Velcro" fasteners sewn onto a coupling surface of the sheath. The sheathed stiffeners or padding may thus be applied simply by pressing them onto the outer surface of the elastic bandage already tautingly arranged around the articulation, in a most precise way to ensure their effectiveness.

What is claimed is:

1. An elastic textile implement to be tightly worn over an articulation or part of the body to be protected and/or aided in its mechanical action, made of at least partially of an elastic fabric comprising an elastomeric yarn and substantially non-elastic yarns, conformable around said part or articulation and tautingly fixed thereon by "Velcro" fasteners, hooked portions of which are sewn on a plurality of independently stretchable edge portions of said implement, each edge portion being superimposable to the outer surface of the fabric and anchorable at any position thereon, said conformable elastic fabric being composed of nonelastic and elastomeric yarns and has a dense population of raised yarn loops (M) projecting for a determined height out of said outer surface of the fabric engageable by said hooked "Velcro" portions, characterized in that said loops are of a substantially non-elastic yarn with a count equal to or greater than 150 DECITEX, of a material selected from the group consisting of nylon, polyester and mylar, either in the form of a monofilament or of a multifilament with a number of filaments equal to or less than 10, interwoven with at least another nonelastic yarn and at least an elastomer yarn.

2. An elastic sanitary product or clothing according to claim 1, characterized in that said loops project from the face of the fabric for a height comprised between 1 and 3 mm.

3. A knee-band according to claim 1, consisting of an elongated band (G) of said elastic fabric, having one of its ends (p) point-shaped and the other end dove-tail-shaped, and having a notch, and comprising "Velcro" fastening members (v1, v2, v3) sewn in proximity of the notch and of the tips (v1, v3) of said dove-tail-shaped end.

4. A knee-band (G) according to claim 3, characterized in that comprises a diaphragm portion (g1) of a different elastic fabric of a higher pliability than said elastic fabric forming the rest of the band (G).

5. An elastic belt according to claim 1, consisting of an elongated band (G) of said elastic fabric, first (t1) and second (t2) triangle-shaped tails of said elastic fabric, superimposed on each other and connected along a junction line (u) to one end of said elongated band (G), the tip of each of said two tails having a "Velcro" fastener member (v1, v2) capable of being anchored on any point of the outer surface of said band (G) provided with said dense population of raised yarn loops.

6. An ankle-band or wrist-band according to claim 1, consisting of a cut piece (Ca, Pa) of said elastic fabric with a profile which defines at least three independently stretchable finger or tail portions, the tip of each of said tail portions being provided with a "Velcro" fastener (v1, v2, v3) capable of being anchored on any point of the outer surface of said band (Ca, Pa).

* * * * *